(12) United States Patent
Peart et al.

(10) Patent No.: US 6,509,005 B1
(45) Date of Patent: Jan. 21, 2003

(54) $\Delta^9$ TETRAHYDROCANNABINOL ($\Delta^9$ THC) SOLUTION METERED DOSE INHALER

(75) Inventors: Joanne Peart, Richmond, VA (US); Peter R. Byron, Richmond, VA (US); Aron H. Lichtman, Richmond, VA (US); Billy R. Martin, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/273,766

(22) Filed: Mar. 22, 1999

Related U.S. Application Data

(60) Provisional application No. 60/105,850, filed on Oct. 27, 1998.

(51) Int. Cl.$^7$ .......................... A61L 9/04; A01N 43/16; A61K 31/35

(52) U.S. Cl. ........................................ 424/45; 514/454

(58) Field of Search ............................. 424/45, 46, 43; 514/454

(56) References Cited

U.S. PATENT DOCUMENTS

| | | | | |
|---|---|---|---|---|
| 4,087,546 A | * | 5/1978 | Archel et al. | 424/283 |
| 4,087,547 A | * | 5/1978 | Archer et al. | 424/283 |
| 4,464,378 A | * | 8/1984 | Hussain | 424/260 |
| 4,476,140 A | * | 10/1984 | Sears et al. | 424/283 |
| 4,635,651 A | * | 1/1987 | Jacobs | 131/270 |
| 4,847,290 A | * | 7/1989 | Burstein | 514/454 |
| 5,492,688 A | * | 2/1996 | Byran et al. | 424/45 |
| 5,502,076 A | * | 3/1996 | Dixit et al. | 514/510 |
| 5,538,993 A | * | 7/1996 | Mechoulam et al. | 514/454 |
| 5,653,961 A | * | 8/1997 | McNally et al. | 424/45 |
| 5,683,676 A | * | 11/1997 | Akehurst et al. | 424/45 |
| 5,736,124 A | * | 4/1998 | Akehurst et al. | 424/45 |
| 5,776,433 A | * | 7/1998 | Tzou et al. | 424/45 |
| 5,804,592 A | * | 9/1998 | Volicer | 514/454 |
| 5,916,540 A | * | 6/1999 | Akehurst et al. | 424/45 |
| 5,922,306 A | * | 7/1999 | Akehurst et al. | 424/45 |
| 5,976,574 A | * | 11/1999 | Gordon | 424/489 |
| 5,980,867 A | * | 11/1999 | Tzou et al. | 424/45 |
| 5,981,572 A | * | 11/1999 | Ellis et al. | 514/456 |
| 5,985,248 A | * | 11/1999 | Gordon et al. | 424/46 |
| 6,001,336 A | * | 12/1999 | Gordon | 424/46 |
| 6,017,963 A | * | 1/2000 | Alfonso et al. | 514/646 |
| 6,039,932 A | * | 3/2000 | Govind et al. | 424/45 |

OTHER PUBLICATIONS

Moren, Int. J. Pharm. 1:213–218 (1978).
Bell, J. Pharm Pharmac. 25:32P–36P (1973).
Tzou, Respiratory Drug Delivery VI, pp. 493–494 (1998).
Olson et al., J. Pharm Pharmacol., 28:86 (1976).
Tashkin, Am. Ref. Resp. Dis. 115:57–65 (1977).
Lichtman, Eur. J. Pharmac. 399:141–149 (2000).

Dalby, R.N., et al.; Medical Devices for the Delivery of Therapeutic Aerosols to the Lungs; Inhalation Aerosols: Physical and Biological Basis for Therapy; Lung Biology in Health and disease, vol. 94, pp. 411–451, 1996.

Gill, E.W., et al.; Blood and Brain Levels of Delta1–tetrahydrocannibinol in mice—The effect of 7–hydroxy–delta1–tetrahydrocannabinol; Biochemical Pharmacology, vol. 23, pp 1140–1143, 1974.

Ross, S., et al.; Constituents of *Cannabis Sativa* L. XXX-VIII; A Review of the Natural Constituents: 1980–1994; Zagazig J Pharm Sci, Dec., 1995; vol. 4, No. 2, pp. 1–10.

Tashkin, DP, et al., Subacute Effects of Heavy Marihuana Smoking on Pulmonary Function in Healthy Men; New Eng. J of Med. 294:125–129, Jan. 15, 1976.

Turner, et al., Constituents of *Cannabis sativa* L. XVIII—Electron Voltage Selected Ion Monitoring Study of Cannabinoids; Biomedical Mass Spectrometry, vol., 7, No. 6, 1990 pp. 247–256.

Maurer et al.; Delta9 tetrahydrocannabinol Shows Antispastic and Analgesic Effects in a Single Case Double–blind Trial; Eur Arch Psychiatry Clin Neurosci 240:1–4, 1990.

Asgharian, B., Wood, r. & Schlesinger, R.B. (1995). Empirical modeling of particle deposition in the alveolar region of the lungs: A basis for interspecies extrapolation. Fund Appl toxicol, 27, 232–238.

Barnett, C., Chiang, C., Perez–Reyes, M. & Owens, S. (1982). Kinetic study of smoking marijuana. J. Pharmacokin Biopharm, 10, 495–506.

Byron, P.R. (1994) Dosing reproducibility from experimental albuterol suspension metered–dose inhalers. Pharm Res, 11, 580–4.

Chiang, C.W. & Barnett, G. (1984). Marijuana effect and delta–9tetrahydrocannabinol plasma level. Clin Pharmacol Ther, 36–234–238.

Christensen, H.d., Freudenthal, R.I., Gidley, J.T., Rosenfeld, R., Boegli, G., Testino, L., Brine, D.R., Pitt, C.G., & Wall, M.E., (1971) Activity of Delta8–and Delta–9–tetrahydrocannabinol and related compounds in the mouse. Science, 172, 165–167.

(List continued on next page.)

*Primary Examiner*—Dameron L. Jones
*Assistant Examiner*—Lauren Q. Wells
(74) *Attorney, Agent, or Firm*—Whitham, Curtis & Christofferson, P.C.; Michael J. Rafa

(57) ABSTRACT

The present invention provides therapeutic formulations for solutions of $\Delta^9$-tetrahydrocannabinol ($\Delta^9$ THC) to be delivered by metered dose inhalers. The formulations, which utilize non-CFC propellants, provide a stable aerosol-deliverable source of $\Delta^9$ THC for the treatment of various medical conditions, such as: nausea and vomiting associated with chemotherapy; muscle spasticity; pain; anorexia associated with AIDS wasting syndrome; epilepsy; glaucoma; bronchial asthma; and mood disorders.

12 Claims, 1 Drawing Sheet

Figure 1:
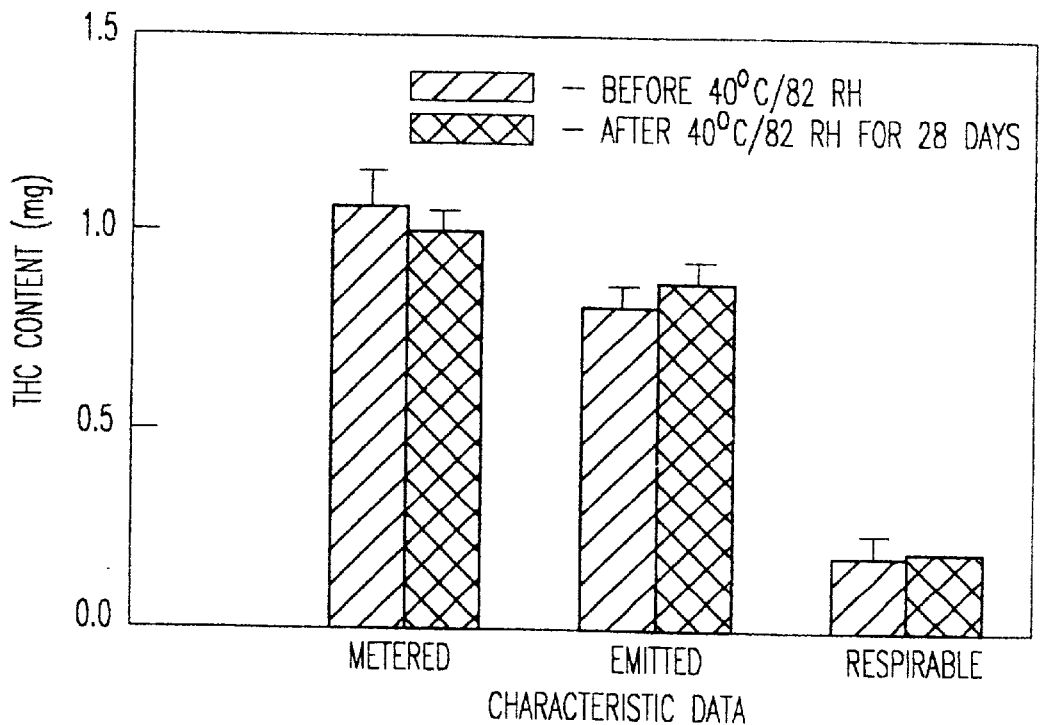

Compton, D., Aceto, M., Lowe, J. & Martin, B. (1996) In vivo characterization of a specific cannabinoid receptor antagonist (SR141716A): inhibition of delta 9–tetrahydrocannabinol–induced responses and apparent agonist activity. J. Pharmacol Exp. Ther, 277, 586–594.

Compton, D.R., Rice, K.C., De Costa, B.R., Razdan, R.K., Melvin, L.S., Johnson, M.R. & Marin, B.R. (1993). Cannabinoid structure–activity relationships: Correlation of receptor binding and in vivo activities. J. Pharmacol Exp Ther, 265, 218–226.

Cone, E. & Huestis, M., (1993). Relating blood concentrations of tetrrahydrocannabinol and metabolites to pharmacologic effects and time of marihuana usage. Ther Drug Mon, 15, 527–532.

D'Amour, F.E. & Smith, D.L. (1941) A method for determining loss of pain sensation. J. Pharm Exp Ther, 72, 74–79.

Ford, R.D., Balster, R.L., Dewey, W.L., & Beckner, J.S., (1977). Delta 9–THC and 11–OH–delta 9–THC: Behavioral effects and relationship to plasma and brain levels. Life Sci., 20, 1993–20004.

Gill, E. W. & Jones, J. (1972) Brain levels of delta 1–tetrahydrocannabinol and its metabolites in mice–correlation with behavior, and the effect of the metabolic inhibitors SKF 525A and piperonyl butoxide. Biochem. Pharmacol., 21, 2237–2248.

Gupta, P.K. & Hickey, A. J. (1991). Contemporay approaches in aerosolized drug delivery to the lungs. J. Controlled release, 17, 129–148.

Henderson, R., Tennant, F., & Guerney, R. (1972) Respitory manifestations of hashish smoking. Arch Otol, 95, 248–251.

Hiller, F.C., Wison, F.J.J., Mazumder, M.K., Wison, J.D. & Bone, R.C., (1984) Concentration and particle size distribution in smoke from marijuana cigarettes with different delta 9–tetrahydrocannabinol content. Fundam Appl Toxicol, 4, 451–454.

House–of–Lords–Select–Committee–on–Science–and–Technology (1998). Ninth Report. Cnnabis: The Scientific and Medical Evidence.

Huber, G.L., Simmons, G.A., McCarthy, C.R., Cutting, MB., Laguarda, R. & Pereira, W. (1975) Depressant effect of marijuana smoke on antibactercidal activity of pulmonary alveolar macrophages. Chest, 68, 769–73.

Huestis, M.A., Sampson, A.H., Holicky, B.J., Henningfield, J.E. & Cone, E.J. (1992) Characterization of the absorption phase of marijuana smoking. Clin Pharmacol Ther, 52, 31–41.

Johansson, E., Ohlsson, A., Lindgren, J.E., Agurell, S., Gillespies, H. & Hollister, L.E. (1987) Single–dose kinetics of deuterium–labelled cannabinol in man after intravenous adminsitration and smoking. Biomed Envirom Mass Spectrum, 14, 495–499.

Lichtman, A.H., Peart, J., Poklis, J.L., Bridgen, D.T., Razdan, R.K., Wilson, D.M., Poklis, A., Meng, Y., Byron, P.R. & Martin, B.R. (2000) Pharmacological evaluation of aerosolized cannabinoids in mice. Eur J. Pharmacol, 399, 141–149.

Lichtman, A.H., Poklis, J.L., Poklis, A., Wilson, D.M. & Martin, B.R. (2001) The pharmacological activity of inhalation exposure to maijuana smoke in mice. Drug Alc Depend 63, 107–116.

Little, P.J., Compton, D.r., Johnson. MR., Melvin, L.S. & Martin, B.R. )1988) Phamrmacology and stereoselectivity of structally novel cannabinoids in mice. J. Phaarmacol Exp Ther, 247, 745–747.

Mattes, R.D., Shaw, L.M., Edling–Owens, J., Engleman, K. & Elsohly, M.A. (1993) Bypassing the first–pass effect for the therapeutic use of cannabinoids. Pharmacol Biochem Behav, 44, 745–747.

Mathias, P., Tashkin, DP., Marques–Magallanes, J.A., Wilkins, J.N. & Simmons, M.S. (1997) Effects of Varying Marijuana Potency on Depositionof Tar and Delta 9–THC in the Lung During Smoking. Pharmacol Biochem Behav. 58, 1145–1150.

Ohlsson, A., Lindgren, J.E., Wahlem, A., Agurell, S., Hollister, L. E. & gillespie, H.K. (1980) Plasma delta–9 tetrahydrocannabinol concentrations and clinical effects after oral and intravenous administration and smokin. Clin Pharmacol Ther, 28, 409–16.

Ohlsson, A., M. Widman, M., Carlsson, S., Ryman, t., & Strid, C. (1980) Plasma and brain levels of delta 6–THC and seven monooxygenated metabolites correlated to the cataleptic effect in the mouse. Acta Pharmacol. Et Toxicol., 47, 308–317.

Perlin, E., Smith, C.G., Nichols, A.I., Almirez, r., Flora, K.P., Cradock, J.C. & Peck, C.C. (1985) Disposition and bioavailability of various fourmulations of tetrahydrocannabinol in the rhesus monkey,. J. Pharm Sci, 74, 171–174.

rinaldi–Carmona, M., Barth, F., Heaulme, M., Shire, D., Calandra, B., Congy, C., Martinez, S., Muruani, J., Neliat, G., Caput, D., Ferrara, P., Soubrie, P., Breliere, J.C., & Lefur, G. (1994) SR141716A, a potent and selective anatagonist of the brain cannabinoid receptor. GEBS Lett, 350, 240–244.

Schlesinger, R.B. (1985) Comparative deposition of inhaled aerosols in experimental animals and humas a review. J. Toxical Environ Health, 15, 197–214.

USP (2000) Physical Tests and Determinations. <601> Aerosols, meterd–dose inhalers, and dry powder inhalers. In United States Pharmacopeia (USP 24) pp. 1895–1912. Philadelphia, PA: National Publishing.

Vachon, L., Robins, A. & Gaensler, E.A. (1976) Airways response to aerosolized delta 9–tetrahydrocannabinol: preliminary report. In The Therapeutic potential of marijuana. Ed. Cohem, S. & Stillman, R.C. pp 111–121. New York: Plenum Medical Book Company.

Vaswani, S.K. & Crticos, P.S. (1998) Metered dose inhaler: past, present, and future. Ann Allergy Asthma Innuol, 80, 11–9; quiz 19–20.

Long–Term Efficacy and Safety of Dronabinol for Aquired Immunodeficiency Syndrome–Associated Anorexia, Journal of Pain and Symptom Management; vol. 14 No. 1 Jul. 1997 pp 7–14.

Dronabinol as a Treatment for Anorexia Associated with Weight Loss in Patients with AIDS; Journal of Pain and Symptom Management; vol. 10 No. 2; Feb. 1995; pp 89–97.

Efficacy of tetrahydrocannabinol in patients refractory to standard antiemetic therapy; Investigational New Drugs 6:243–246; (1988); Mary McCabe, Frederick P. Smith, John S. Macdonald, Paul V. Woolley, Deborah Goldberg, and Philip S. Schien; Divisional of Medical Oncology, Vincent T. Lombardi Cancer Research Center, Dept. of Medicine. Georgetown University.

Tetrahydrocannabinol for Refractory Vomiting Induced by Cancer Chemotherapy; JAMA Mar. 28, 1980–vol. 243, No. 12.

Antiemetics–Sallan, et al., The New England Journal of Medicine; Jan. 17, 1980; vol. 302 No. 3; pp 135–138.

Delta–9–Tetrahydrocannabinol as an Antiemetic for Patients rceiving Cancer Chemotherapy; Dec. 1979; Annals of Internal Medicine; vol. 91 No. 6; pp. 825–830.

Delta–9–Tetrahydrocannabinol as an Antiemetic in Cancer Patients Receiving High–Dose Methotrexate; Dec. 1979; Annals of Internal Medicine; vol. 91 No. 6; pp. 820–824.

Analgesic effect of Delta–9–tetrahydrocannabinol; Dept. of Psychiatry and Internal Medicine, University of Iowa College; Feb.–Mar. 1975; pp. 139–143.

Analgesic Properties of delta–9–tetrahydrocannabinol and codiene; Depart., of Psychiatry and Medicine, University of Iowa; published Mar. 29, 1975; pp 84–89.

The effect of orally and rectally administered 9–tetrahydrocannabinol on spasticity: A pilot study with 2 patients; Institute of Pharmacy, University of Bern; International Journal of Clinical Pharmacology and Therapeutics, vol. 34 No. 10–1996 (446–452).

Delta–9–THC in the Treatment of Spasticity Associated with Multiple Sclerosis; Dept. of Psychiatry at U.C.L.A; 1988 Hawthorne Press; pp. 39–50.

Workshop on the medical utility of marijuana. National Institutes of Health, Aug. 1997.

Olsen, J.L., Lodge, J.W., Shapiro, B.J. and Tashkin, D.P. (1976). An inhalation aerosol of $\Delta^9$–tetrahydrocannabinol. *Journal of Pharmacy and Pharmacology,* 28:86.

Thornton, Jacqul, (Jun. 13, 1999). Cannabis inhalers in first legal health test. *Electronic Telegraph, UK News Summary,* www.telegraphco.UK, Issue 1479.

Tashkin, D.P., Reiss, S., Shapiro, B.J., Calvarese, B., Olsen, J.L. and Lodge, J.W. (1977). Bronchial effects of aerosolized $\Delta^9$–tetrahydrocannabinol in healthy and asthmatic subjects. *American Review of Respiratory Disease.* 115:57–65.

Williams, S.J., Hartley, J.P.R., Graham, J.D.P. (1976). Bronchodilator effect of $\Delta^1$–tetrahydrocannabinol administered by aerosol to asthmatic patients. *Thorax. 31:720–723.*

* cited by examiner

Δ⁹ TETRAHYDROCANNABINOL (Δ⁹ THC) SOLUTION METERED DOSE INHALER

CROSS REFERENCE TO RELATED APPLICATION

This application is a continuation-in-part of U.S. provisional application Ser. No. 60/105,850 filed Oct. 27, 1998, and the complete contents of that application are incorporated herein by reference.

Funding for the research which led to this invention was provided in part by the United States Government in grant # DA 02396 from the National Institutes of Health and the government may have certain rights in this invention.

DESCRIPTION

BACKGROUND OF THE INVENTION

1. Field of the Invention

The invention is generally related to the therapeutic use of $\Delta^9$ Tetrahydrocannabinol ($\Delta^9$ THC). In particular, the invention provides a metered dose inhaler (MDI) for the aerosol administration of $\Delta^9$ THC to patients suffering from nausea and vomiting associated with cancer chemotherapy, muscle spasticity, pain, anorexia associated with AIDS wasting syndrome, epilepsy, glaucoma, bronchial asthma, mood disorders, and the like.

2. Background Description

"Medical Marijuana" is a timely and controversial subject that is currently receiving widespread public attention. While marijuana is usually thought of as an illegal "recreational" drug, it also has a long history as a medicine. In 1997, the National Institutes of Health (NIH) released a review of the scientific data concerning potential therapeutic uses for marijuana. In that review, the NIH found that marijuana may indeed have beneficial medicinal effects and recommended that researchers develop alternative dosage forms for the drug, such as a "smoke free" inhaled delivery system (1). Table 1 summarizes the findings of several studies (references 2–18) that have documented therapeutically beneficial medicinal uses of the major active component of marijuana, $\Delta^9$ tetrahydrocannabinol ($\Delta^9$ THC).

TABLE 1

The Use of $\Delta^9$THC for the Treatment of Assorted Clinical Conditions

| Condition and Number of Patients | Administration Route and Dose | Findings | Reference |
| --- | --- | --- | --- |
| AIDS-associated anorexia and cachexia; 94 patients; 12 months | Oral placebo, 2.5 mg THC once or twice daily increasing to 20 mg daily | Long term THC treatment was well tolerated; THC improved appetite and only tended to increase weight compared to controls | Beal et al., 1997 |
| AIDS-associated anorexia and cachexia; 139 patients; 42 days | Oral placebo or 2.5 mg THC twice daily | 57% and 69% of vehicle and THC patients were evaluable for efficacy. Appetite increased 38% over baseline for THC group compared to only 8% for the placebo group. THC also decreased nausea. No significant changes were found between the groups for weight change. | Beal et al., 1995 |
| Nausea and emesis due to cancer chemotherapy; 36 patients who had experienced severe nausea and vomiting that was refractory to prochlorperazine or thiethylperazine | Oral THC, 15 mg/m² | Reduction in chemotherapy-induced nausea and vomiting in 64% of patients given THC compared to prochloperazine; side effects included dysphoria; authors recommend initial THC dose of 5 mg/m² | McCabe et al., 1988 |
| Nausea and emesis due to cancer chemotherapy; 53 patients which were refractory to other antiemetics | Oral 5 or 15 mg/m² THC four times per day | 72% of patients exhibited a THC-induced partial or complete blockade of vomiting | Lucas and Laszlo, 1980 |
| Nausea and emesis due to cancer chemotherapy; 84 patients | Oral 10 mg/m² THC of prochloperazine | THC more effective than prochloperazine | Sallan et al., 1980 |
| Nausea and emesis due to cancer chemotherapy; 116 patients | Oral 15 mg THC, 10 mg prochloperzine or placebo | Equal antiemetic effects between THC and prochlorperazine, effects of each greater than placebo; considerably more CNS side effects with THC than prochlorperazine | Frytak et al., 1979 |
| Nausea and emesis due to cancer chemotherapy; 15 patients | Oral placebo or 10 mg/m² THC every 3 hours for a total of 5 doses, THC (17 mg) laced cigarettes or placebo were given if vomiting occurred | 93% patients had a reduction in nausea and vomiting, 53% had an excellent response, 40% had a fair response; plasma THC levels 7.1 ± 6.9 (mean ± SD) ng/ml. Side effects included sedation, tachycardia, few other side effects | Chang et al., 1979 |
| Pain due to advanced cancer; 10 patients | Oral placebo and 5, 10, 15 or 20 mg THC | Pain relief, elevated mood, appetite stimulation, drowsiness, slurred speech, mental clouding | Noyes, et al, 1975 |
| Pain due to advanced cancer; | Placebo, 10 and 20 mg THC, and | THC produced a similar degree | Noyes et al. 1975 |

TABLE 1-continued

The Use of Δ⁹THC for the Treatment of Assorted Clinical Conditions

| Condition and Number of Patients | Administration Route and Dose | Findings | Reference |
|---|---|---|---|
| 34 patients | 60 and 120 codeine | of analgesia, with greater potency than codeine. THC CNS side effects included sedation, mental clouding, ataxia, and disorientation | |
| Spasticity related to multiple schlerosis; 2 patients | Oral 10 or 15 mg THC, rectal dose of 5 or 10 mg THC | Improvement in passive mobility and walking ability | Brenneisen et al., 1996 |
| Spasticity related to multiple schlerosis; 13 patients | Oral 2.5 to 15 mg THC once or twice daily or placebo | Significant subjective improvement in spasticity at 7.5 mg THC and higher, no significant improvement in objective measurements | Ungerleider et al., 1987 |
| Spasticity related to multiple schlerosis; 8 patients, single blind | Oral 5 to 15 mg THC | 5 of 8 patients had mild subjective improvement in tremor. 2 of 8 patients had both objective and subjective improvement | Clifford, 1983 |
| Spasticity related to multiple schlerosis; 9 patients | Placebo, or 5 or 10 mg THC | Decrease in spasticity compared to placebo treatment, minimal side effects | Petro and Ellenberger, 1981 |
| Spasticity and pain due to spinal cord injury; 1 patient | Oral placebo, THC (5 mg), or codeine (50 mg) | THC and codeine had analgesic effect compared to the placebo treatment. THC had a beneficial effect on spasticity whereas codeine did not | Maurer et al., 1990 |
| Glaucoma, 6 patients | Oral placebo or 5, 10, 15 and 20 mg THC | Pain relief elevated mood, appetite stimulation, drowsiness, slurred speech, mental clouding | Merritt et al, 1980 |
| Ten subjects with normal intra ocular pressure | Intravenous THC (0.022 or 0.044 mg/kg) | Decreased intra ocular pressure by a mean of 37% | Cooler and Gregg, 1977 |
| Nausea and emesis due to cancer chemotherapy; refractory to other antiemetics | Oral 10 mg/m² THC or placebo | In 20 courses of THC, 5 resulted in no vomiting, 9 resulted in a reduction of vomiting, 3 resulted in no decrease in vomiting, and 2 were unevaluable. THC was significantly better than placebo in decreasing vomiting. | Sallan et al., 1975 |

When marijuana is used illegally as a recreational psychoactive drug, the active ingredient Δ⁹ THC is usually delivered to the lungs as an impure non-pharmaceutical aerosol in the form of marijuana smoke. Aerosolized Δ⁹ THC in the inhaled smoke is absorbed within seconds and delivered to the brain efficiently. Table 2 and references 19–20 describe the pharmacokinetics of the administration of Δ⁹ THC. As can be seen, inhalation is the preferred route of delivery for Δ⁹ THC. When compared to oral delivery, inhalation provides a more rapid onset of pharmacological action and peak plasma levels. The effects achieved via inhalation are comparable to those achieved when the drug is administered intravenously, but inhalation is a much less invasive technique.

TABLE 2

Pharmacokinetics of Δ⁹ THC Given Orally, Intravenously or by Smoking

| Route | Dose | % Dose in Plasma | Onset of Pharmacological Action | Peak Plasma Levels | References |
|---|---|---|---|---|---|
| Oral, sesame oil in gelatin capsules | 2.5, 5, or 10 mg | 10 to 20% | 0.5 to 1 hour | 120–480 min | (PDR, 1995) |
| Oral, in cookies | 20 mg | 4 to 12% | 120–180 min | 60–90 min | (Ohlsson, et al., 1980) |
| Intravenous, bolus | 5 mg | 100% | 10 min | 3 min | (Ohlsson, et al., 1980) |
| Smoking (THC lost to side stream smoke and pyrolysis | 13 mg | 8 to 24% | 10 min | 3 min | (Ohlsson, et al., 1980) |

Currently, the sources of $\Delta^9$ THC for patients who could benefit from the drug are very limited. An oral form of $\Delta^9$ THC (MARINOL) is marketed as a treatment for nausea and vomiting related to cancer chemotherapy, and as an appetite stimulant in patients suffering from AIDS wasting syndrome. In MARINOL, pharmaceutical grade $\Delta^9$ THC is dissolved in sesame oil, encapsulated in gelatin capsules and delivered orally. However, when the drug is taken orally, the absorption is slower and more variable than when inhaled, with an onset of action between 30 minutes and 2 hours (Table 2). Alternatively, some cancer patients do manage to obtain and smoke marijuana in order to alleviate such conditions as nausea and vomiting due to chemotherapy. This is, however, technically illegal and is thus obviously a less than ideal treatment protocol. There is no currently available pharmaceutically acceptable aerosol form of $\Delta^9$ THC.

It would be advantageous to have available a form of pharmaceutical grade $\Delta^9$ THC that could be administered as an aerosol. This would provide a means for rapid uptake of the drug without resorting to the illegal practice of smoking marijuana. Also, the potential adverse side effects encountered by smoking marijuana would be avoided. Further, an aerosol preparation of pharmaceutically pure $\Delta^9$ THC could be administered in known, controlled dosages.

In 1976, Olsen et al. described a chlorofluorocarbon (CFC) propelled MDI formulation of $\Delta^9$ THC (21). However, $\Delta^9$ THC is known to deteriorate during storage, and the stability of $\Delta^9$ THC in this formulation is suspect. In addition, the ethanol content in this formulation was so high (~23%) as to create an aerosol with droplets too large to be effectively inhaled (22). The $\Delta^9$ THC CFC formulations were tested for use in treating asthma but were shown to be only moderately effective (23, 24). Moreover, CFC propellants have since been banned so that such a formulation is now useless. It would clearly be advantageous to develop a new aerosol formulation in which the $\Delta^9$ THC is stable, the droplets are of a size that can be effectively inhaled, and which utilizes a non-CFC propellant.

SUMMARY OF THE INVENTION

It is an object of the present invention to provide a stable aerosol-dispensable pharmaceutical composition comprising a non-CFC propellant and a pharmaceutically effective concentration of $\Delta^9$ THC. More particularly, it is an object of the present invention to provide a stable aerosol-dispensable pharmaceutical composition comprising a hydrofluoroalkane propellant, (for example, HFA 227 or HFA 134a) and $\Delta^9$ THC. The propellant is present in the range of approximately 78 to 100% by weight, and more particularly the propellant is present in the range of approximately 85 to 100% by weight. An organic solvent such as ethanol can be used to assist in solubilizing the $\Delta^9$ THC in the propellant but is not required. If a solvent is used, preferably less than 20% by weight will be required, and most preferably less than 15% by weight will be required. The pharmaceutically effective concentration of $\Delta^9$ THC is preferably in the range of 0.05 to 10% by weight, and most preferably in the range of 0.1 to 6% by weight. The pharmaceutical composition of the present invention can be used to treat a variety of medical conditions including nausea and vomiting associated with cancer chemotherapy, muscle spasticity, pain, anorexia associated with AIDS wasting syndrome, anorexia associated with cancer chemotherapy, epilepsy, glaucoma, bronchial asthma, mood disorders, migraine headaches.

DETAILED DESCRIPTION OF THE DRAWINGS

FIG. 1. $\Delta^9$ THC MDI characterization summary before and after storage at 40° C. and 82% relative humidity (RH).

FIG. 2. Generalized schematic drawings of a $\Delta^9$ THC MDI.

DETAILED DESCRIPTION OF A PREFERRED EMBODIMENT OF THE INVENTION

The instant invention provides a series of non-ozone depleting pressurized metered dose inhaler formulations of $\Delta^9$ THC. In preferred embodiments of the invention, the formulations contain the pharmaceutically acceptable, non-ozone depleting hydrofluoroalkane propellants HFA 134a (1,1,1,2-tetrafluoroethane) and HFA 227 (1,1,1,2,3,3,3-heptafluoropropane), or a mixture thereof.

When the propellant is a hydrofluoroalkane, it has been discovered that the propellant may be used with or without a solvent such as ethanol. Higher percentages of solvent generally allow higher levels of dissolution of $\Delta^9$ THC. However, higher percentages of solvent also cause droplet size to increase. In preferred embodiments of the invention, the range of propellant compositions, as shown in Table 3, may be from 100% propellant and 0% solvent to 85% propellant and 15% solvent. Within this range of percentages, pharmaceutically useful concentrations of $\Delta^9$ THC can be achieved and droplet size is still small enough (<5.8 $\mu$m) to provide excellent aerosol delivery of the drug. While these ratios reflect preferred embodiments of the invention, it will be recognized by those of skill in the art that the exact ratio of propellant to solvent (e.g. ethanol) may vary according to the desired final concentration of $\Delta^9$ THC and droplet size. Any ratio of propellant to solvent that results in appropriate sized droplets and adequate dissolution of the $\Delta^9$ THC may be used in the practice of this invention, and this will generally be in the range of from 100 to 80% propellant and 0 to 20% solvent. It is expected that a wide variety of solvents, such as ethanol, propanol, propylene glycol, glycerol, polyethylene glycol, etc. may be used in the preparation of formulations contemplated by this invention.

Those skilled in the art will also recognize that the "respirable dose" (or mass of $\Delta^9$ THC in particles with aerodynamic diameters small enough to be delivered to and absorbed by the lungs) FIG. 1) may be increased by choosing MDI spray nozzles of different design and smaller orifice diameters. Respirable doses may also be increased by extending the mouthpiece of the MDI in such a way as to create an integral or separate aerosol spacer or reservoir attached to the mouthpiece of the MDI. This promotes an increase in droplet evaporation and hence in the percentage of the dose in smaller "respirable" particles or droplets. Generally, the optimal size of a respirable droplet is less than 10 $\mu$m in size.

TABLE 3

Apparent Solubility of $\Delta^9$THC in Ethanol/HFA Propellant Blends

| Formulation | Mass (g) of $\Delta^9$THC in Sample | Mass (g) of Formulation Sampled | Apparent Solubility Mean (±SD) | Comments |
|---|---|---|---|---|
| $\Delta^9$THC in 100% HFA 134a | 0.000240 | 0.1071 | 0.224% w/w (±0.063) | Excess $\Delta^9$THC added to propellant blend (in pressurized MDI). Solubility sample removed using puff absorber. n = 5 |
| $\Delta^9$THC in 5% Ethanol/95% HFA 134a | 0.00144 | 0.0914 | 1.585% w/w (±0.321) | As above |

TABLE 3-continued

Apparent Solubility of $\Delta^9$THC in Ethanol/HFA Propellant Blends

| Formulation | Mass (g) of $\Delta^9$THC in Sample | Mass (g) of Formulation Sampled | Apparent Solubility Mean (±SD) | Comments |
|---|---|---|---|---|
| $\Delta^9$THC in 10% Ethanol/90% HFA 134a | 0.00363 | 0.1036 | 3.511% w/w (±0.249) | As above |
| $\Delta^9$THC in 15% Ethanol/85% HFA 134a | 0.00536 | 0.1098 | 4.883% w/w (±0.224) | As above |
| $\Delta^9$THC in 100% HFA 227 | 0.00021 | 0.1451 | 0.147% w/w (±0.008) | As above |
| $\Delta^9$THC in 5% Ethanol/95% HFA 227 | 0.00134 | 0.0979 | 1.339% w/w (±0.169) | As above |
| $\Delta^9$THC in 10% Ethanol/90% HFA 227 | 0.00454 | 0.1267 | 3.240% w/w (±0.161) | As above |
| $\Delta^9$THC in 15% Ethanol/85% HFA 227 | 0.00623 | 0.1062 | 5.940% w/w (±0.191) | As above |

A distinct advantage of the present formulations is that, surprisingly, the use of surface active agents or "surfactants" as valve lubricants and solubilizers is not necessary. This is in contrast to the invention of Purewal and Greenleaf (European Patent 0,372,777; reference #25) which provides HFA 134a/ethanol mixtures to produce stable formulations of pharmaceuticals in the presence of lipophilic surface active agents. Lipophilic surface active agents are incorporated in that invention in order to suspend undissolved material and to ensure adequate valve lubrication of the MDI. Without adequate valve lubrication, the useful life of the MDI and its ability to deliver an accurate dose of drug are severely attenuated. However, probably due to the inherent lubricity of the formulations of the present invention, the use of such surface active agents is unnecessary. This simplifies the composition and thus is an advantage with respect to cost and the elimination of potentially deleterious interactions between components of the formulations and the agents.

A major consideration in the formulation of any drug is its stability. $\Delta^9$ THC is known to deteriorate upon storage so that the effective concentration decreases and the purity is vitiated. The stability of the formulations of the present invention were tested according to accelerated storage testing protocols. The results are given in FIG. 1 and Tables 4A and 4B. The formulations of the present invention were shown to be stable with respect to the release of aerosolized $\Delta^9$ THC in reproducible doses following accelerated storage testing. Apparently, the containment of $\Delta^9$ THC in solution in the non-aqueous formulations of the present invention is excellent with respect to chemical degradation, making possible the construction of a multidose inhaler with a good shelf life prognosis.

Further, lipophilic materials like $\Delta^9$ THC are generally known to partition into the elastomers of the valves in MDI formulations. ($\Delta^9$ THC is highly lipophilic as reflected in its octanol:water partition coefficient of 6000: 1). Over time, this partitioning results in a decrease in the emmited or delivered dose of a lipophilic drug. Thus, this phenomenon also decreases the useful shelf-life of such preparations. However, the data presented in FIG. 1 and Table 4 show that this is not the case with the formulations of the present invention. The emitted or delivered doses were constant over the time period tested. This may be due to the somewhat surprising preference of $\Delta^9$ THC for the formulation itself, rather than for the valve elastomers.

TABLE 4A

Formulation and aerosol characteristics of $\Delta^9$ THC pressurized metered dose inhalers in ethanol/hydrofluoroalkane (HFA) propellant blends

| | Formulation (% w/w) | | | |
|---|---|---|---|---|
| Inhaler | $\Delta^9$ THC | Ethanol | Propellant | Description |
| 1 | 0.13% | ~5% | 95% HFA 134a | 3/98 Pale Yellow Solution |
| 2 | 0.13% | ~5% | 95% HFA 227 | 3/98 Pale Yellow Solution |
| 3 | 0.12% | ~5% | 95% HFA 134a | 3/98 Pale Yellow Solution |
| 4 | 0.18% | ~5% | 95% HFA 134a | 3/98 Pale Yellow Solution |
| 5 | 0.27% | ~5% | 95% HFA 227 | 3/98 Pale Yellow Solution |
| 6 | 0.25% | ~5% | 95% HFA 134a | 3/98 Pale Yellow Solution |
| 7 | 0.57% | ~5% | 95% HFA 134a | 3/98 Yellow Solution |
| 8 | 0.58% | ~5% | 95% HFA 227 | 3/98 Yellow Solution |
| 9 | 0.49% | ~5% | 95% HFA 134a | 3/98 Yellow Solution |
| 10 | 1.02% | ~5% | 95% HFA 134a | 3/98 Yellow Solution |
| 11 | 1.11% | ~5% | 95% HFA 227 | 3/98 Yellow Solution |
| 12 | 0.97% | ~5% | 95% HFA 134a | 3/98 Yellow Solution |
| SS* #1 Initial | 1.07% | 4.94% | 94.0% HFA 134a | 6/98 Yellow Solution |
| SS* #1 after 28 days at 40° C./82% RH** | 1.07% | 4.94% | 94.0% HFA 134a | 7/98 Yellow Solution |
| SS* #2 after 21 days at 40° C./82% RH** | 1.00% | 5.01% | 95% HFA 134a | 7/98 Yellow Solution |
| SS* #3 Modified Actuator*** | 1.02% | 5.15% | 93.8% HFA 134a | 10/98 Yellow Solution |

[a]Mean (Standard Deviation) of five determinations.
[b]Mass of $\Delta^9$ THC aerosol particles <5.8 μm aerodynamic diameter
*SS: Stability Sample
**RH: relative humidity
***Approximate spray nozzle diameter = 0.2 mm.

TABLE 4B

Formulation and aerosol characteristics of $\Delta^9$ THC pressurized metered dose inhalers in ethanol/hydrofluoroalkane (HFA) propellant blends

| | Aerosol Characterization | | |
|---|---|---|---|
| Inhaler | Metered Dose (mg)[a] | Emitted Dose (mg)[a] | Fine Particle Dose (mg)[a,b] |
| 11 | 1.72 (0.25) | 1.32 (0.17) | ND |
| 12 | 0.94 (0.23) | 0.97 (0.10) | 0.38 (0.02) |
| SS* #1 Initial | 1.10 (0.07) | 0.90 (0.03) | 0.22 (0.03) |
| SS* #1 after 28 days at 40° C./82% RH** | 1.06 (0.03) | 0.92 (0.04) | 0.23 (0.02) |
| SS* #2 after 21 days at 40° C./82% RH** | 1.02 (0.05) | 0.90 (0.05) | 0.21 (0.02) |
| SS* #3 Modified Actuator*** | ND | ND | 0.40 (n = 1) |

[a]Mean (Standard Deviation) of five determinations.
[b]Mass of $\Delta^9$ THC aerosol particles with <5.8 μm aerodynamic diameter
*SS: Stability Sample
**RH: relative humidity
ND: not determined
***Approximate spray nozzle diameter = 0.2 mm The final concentration of $\Delta^9$ THC in a given formulation may be varied by adjusting the ratio of propellant to solvent and thus the solubility of the $\Delta^9$ THC. Higher percentages of solvent (e.g. ethanol) generally allow a higher amount of $\Delta^9$ THC to be dissolved. For example, in preferred embodiments of the invention, the apparent solubility of $\Delta^9$ THC ranged from 0.147% w/w to 5.94% w/w as the propellant composition varied from 100% HFA 227 to 85% HFA 227 and 15% ethanol. Thus, the dose of $\Delta^9$ THC in a given metered volume may be selected by changing the formulation.

Further, as stated above, the "fine particle dose" or "respirable dose" of a drug dispensed with an MDI is a function of the spray nozzle diameter. In FIG. 1 and Tables 4A and 4B, the spray nozzle diameter is 0.4mm. The "fine particle dose" or "respirable dose" of the formulations of the present invention was shown to be unaffected by storage.

The $\Delta^9$ THC of the present invention is pharmaceutically pure. That is, its form is the nonionized resinous drug substance (6aR-trans)-6a,7,8, 10a-tetrahydro-6,6,9-trimethyl-3-pentyl-6H-dibenzo[b,d]-pyran-1-ol. Although its preferred embodiment in this invention is not a salt or ester, it will be readily understood by those of skill in the art that other appropriate forms of $\Delta^9$ THC may be synthesized (e.g. esters and salts) and thus used in the practice of this invention.

The desired final concentration of $\Delta^9$ THC in a patient's serum will vary from patient to patient depending on, for example, the nature and severity of the condition being treated, and the patient's overall condition, weight, gender and response to the drug, etc. But the desired range will generally be 10–100 ng/ml at 15 minutes following inhalation. The level of $\Delta^9$ THC in a patient's serum can be readily and reliably monitored by gas chromatography/mass spectrophotometry (GC/MS).

The exact treatment protocol to be used may vary from patient to patient depending on the circumstances. For example, in a preferred embodiment of the invention, a patient receiving chemotherapy may have one dose of $\Delta^9$ THC prescribed via inhalation, to be administered 15 minutes before chemotherapy and 4–8 times daily following chemotherapy. In another preferred embodiment, a patient suffering from anorexia associated with AIDS wasting syndrome may have $\Delta^9$ THC by inhalation prescribed 3–5 times daily, 30 minutes before each meal or snack. In other preferred embodiments, a patient suffering form cancer pain, or spasticity related to either multiple sclerosis or spinal cord injury may have $\Delta^9$ THC by inhalation prescribed 3–6 times daily. Those skilled in the art will readily recognize that the treatment protocol may be crafted so as to address the particular needs of each individual patient on a case by case basis.

$\Delta^9$ THC may be used alone or in combination with other medications. Those skilled in the art will readily recognize that, for example, in the case of AIDS wasting syndrome, the patient will likely also be taking drugs that combat the AIDS virus. Similarly, those skilled in the art will readily recognize that patients receiving chemotherapy for cancer may also receive other antiemetics, and cancer patients seeking to relieve pain are likely to receive opioids as well as nonsteroidal anti-inflammatory agents.

Figure 2:
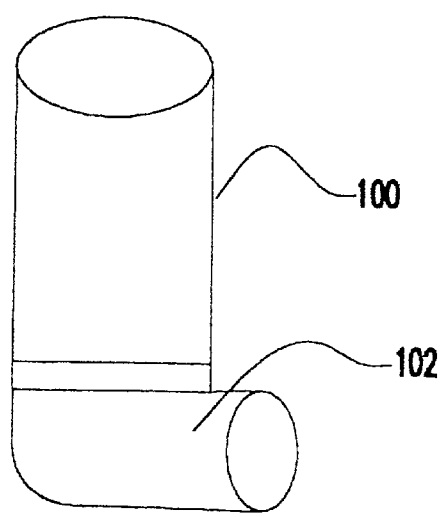

The containers for the formulations of the instant invention may be any that are suitable for the efficacious delivery of aerosol inhalants. Several containers and their method of usage are known to those of skill in the art. For example, MDIs can be used with various dose metering chambers, various plastic actuators and mouthpieces, and various aerosol holding chambers (e.g. spacer and reservoir devices), so that appropriate doses of $\Delta^9$ THC reach and deposit in the lung and are thereafter absorbed into the bloodstream. In addition, a lock mechanism such as that shown in U.S. Pat. No. 5,284,133 to Burns and Marshak, which is herein incorporated by reference, can be used to prevent overdose or unauthorized consumption of $\Delta^9$ THC. FIG. 2 provides a generalized drawing of an MDI containing the composition of this invention and provides the advantage of delivering metered quantities of $\Delta^9$ THC on a repetitive basis. The MDI includes a container 100 for holding the composition and a valve delivery mechanism 102 for delivery of aerosolized $\Delta^9$ THC.

While the invention has been described in terms of its preferred embodiments, those skilled in the art will recognize that the invention can be practiced with modification within the spirit and scope of the appended claims.

REFERENCES

1. Workshop on the medical utility of marijuana. National Institutes of Health, August 1997.
2. Beal, J. A., Olson, R., Lefkowitz, L., Laubenstein, L., Bellman, P., Yangco, B., Morales, J. O., Murphy, R., Powderly, W., Plasse, T. F., Mosdell, K. W.and Shepard, K. W. (1997) Long-term efficacy and safety of dronabinol for acquired immunodeficiency syndrome-associated anorexia. *J Pain. Symptom Manage.* 14:7–14.
3. Beal, J. A., Olson, R., Laubenstein, L., Morales, J. O., Bellman, B., Yangco, B., Lefkowitz, L., Plasse, T. F. and Shepard, K. V. (1995) Dronabinol as a treatment for anorexia associated with weight loss in patients with AIDS *J Pain. Symptom Manage.* 10:89–97.
4. McCabe, M., Smith, F. P., MacDonald, J. S., Wooley, P. V., Goldberg, D. and Schein, P. S. (1988) Efficacy of tetrahydrocannabinol in patients refractory to standard antiemetic therapy. *Invest. New Drugs* 6:243–246.
5. Lucas, V. S. and Laszlo, J. (1980) $\Delta^9$-THC for refractory vomiting induced by cancer chemotherapy. *JAMA* 243:1241–1243.
6. Sallan, S. E., Cronin, C., Zelen, M. and Zinberg, N. E. (1980) Antiemetics in patients receiving chemotherapy for cancer: a randomized comparison of Δ⁹ THC and prochlorperazine. *N Engl. J Med.* 302:135–138. p0 7. Frytak, S., Moertel, C. G., O'Fallon, J. R., Rubin, J., Creagan, E. T., O'C.onnell, M. J., Schutt, A. J. and Schwartau, N. W. (1979) Delta-9-tetrahydrocannabinol as an antiemetic for patients receiving cancer chemotherapy: a comparison with prochlorperazine and a placebo. *Ann. Inter. Med.* 91:825–830.
8. Chang, A. E., Shiling, D. J., Stillman, R. C., Goldgerg, N. H., Seipp, C.A., Barofdky, I., Simon, R. M. and Rosenberg SA (1979) Δ⁹ THC as an antiemitic in cancer patients receiving high-dose methotrexate. *Ann. Internal. Med.* 91:819–824.
9. Sallan, S. E., Zinberg, N. E. and Frei, I. E. (1975) Antiemetic effect of Δ⁹ THC in patients receiving cancer chemotherapy. *New Engl. J. Med.* 293:795–797.
10. Noyes, J. R., Brunk, S. F., Baram, D. A. and Canter, A. (1975) The analgesic properties of Δ⁹ THC and codeine. *J. Clin. Pharmacol.* 15:139–143.
11. Noyes, R., Jr., Brunk, S. F., Baram, D. A. and Canter, A. (1975) Analgesic effect of Δ⁹-tetrahydrocannabinol. *J. Clin. Pharmacol.* 15:139–143.
12. Brenneisen, R., Egli, A., Elosohlly, M. A., Henn, V. and Spiess, Y. (1996) The effect of orally and rectally administered Δ⁹ THC on spasticity: a pilot study with 2 patients. *Int. J. Clin. J. Pharmocol. Ther.* 34:446–452.
13. Ungerleider, J. T., Andyrsiak, T. F. L., Ellison, G. W. and Myers, L. W. (1987) Δ⁹ THC in the treatment of spasticity associated with multiple sclerosis. *Adv. Alcohol Subst. Abuse* 7:39–50.
14. Clifford, D. B. (1983) Tetrahydrocannabinol for tremor in multiple sclerosis. *Ann. Neurol.* 13:669–171.
15. Petro, D. J. and Ellenberger, C. (1981) Treatment of human spasticity with delta 9-tetrahydrocannabinol. *J. Clin. Pharmacol.* 21:413S-416S.
16. Maurer, M., Henn, V., Dittrich, A. and Hofinan, A. (1990) Delta 9-tetrahydrocannabinol shows antispastic and analgesic effects in a single case double-blind trial. *Eur. Arch. Psychiatry Neurol. Sci.* 240:1–4.
17. Merritt, J., Crawford, W., Alexander, P., Anduze, A. and Gelbart, S. (1980) Effects of marihuana on intra ocular and blood pressure in glaucoma. *Opht.* 87:222–228.
18. Cooler, P. and Gregg, J. M. (1977) Effect of delta 9-Δ⁹ THC on intra ocular pressure in humans. *South. Med J.* 70:951–954.
19. PDR (1995) Physician's Desk Reference (49) Montvalek, New Jersey: Medical Economics Data Production Co., pp.2787.
20. Ohlsson, A., Lindgren, J. E., Wahlen, A., Agurall, S., Hollister, L. E. and Gillespie, H. K. (1980) Plasma Δ⁹ THC concentrations and effects after oral and intravenous administration and smoking. *Clin. Pharmacol. Ther.* 28:409–416.
21. Olsen, J. L., Lodge, J. W., Shapiro, B. J. and Tashkin, D. P. (1976) An inhalation aerosol of Δ⁹-tetrahydrocannabinol. *J. Pharmacy and Pharmacol.* 28:86.
22. Dalby, R. N. and Byron, P. R. (1988) Comparison of output particle size distributions from pressurized aerosols formulated as solutions or suspensions. *Pharm. Res.* 5:36–39.
23. Tashkin, D. P., Reiss, S., Shapiro, B. J., Calvarese, B., Olsen, J. L. and Lidgek, J. W. (1977) Bronchial effects of aerosolized Δ⁹- tetrahydrocannabinol in healthy and asthmatic subjects. *Amer. Rev. of Resp. Disease.* 115:57–65.
24. Williams, S. J., Hartley, J. P. R. and Graham, J. D. P. (1976) Bronchodilator effect of delta-9-THC administered by aerosol to asthmatic patients. *Thorax.* 31:720–723.
25. European Patent 0,372,777 (Riker Laboratories). Medicinal aerosol formulations.

We claim:

1. A pharmaceutical composition consisting essentially of 1,1,1,2,3,3,3-heptafluoropropane (HFA 227), Δ⁹-tetrahydrocannabinol, and up to 15 percent by weight of an organic solvent, said Δ⁹-tetrahydrocannabinol and said organic solvent being dissolved in said HFA 227 to form a stable composition, wherein said Δ⁹-tetrahydrocannabinol is present in said composition in concentrations ranging from 0.147% w/w (±0.008) to 5.940% w/w (±0.191).

2. The pharmaceutical composition of claim 1 wherein said Δ⁹-tetrahydrocannabinol is present in pharmaceutically pure form.

3. The pharmaceutical composition of claim 1 wherein the concentration of Δ⁹-tetrahydrocannabniol is sufficient to achieve serum concentration levels in a patient of 10–100 ng/ml fifteen minutes following inhalation.

4. The pharmaceutical composition of claim 1 wherein said organic solvent is ethanol.

5. The pharmaceutical composition of claim 1 wherein said organic solvent is 0% w/w of said stable composition.

6. The pharmaceutical composition of claim 1 wherein said stable composition is surfactant free.

7. A pharmaceutical composition consisting essentially of 1,1,1,2-tetrafluoroethane (HFA 134a), Δ⁹-tetrahydrocannabinol, and up to 15 percent by weight of an organic solvent, said Δ⁹-tetrahydrocannabinol and said organic solvent being dissolved in said HFA 134a to form a stable composition, wherein said Δ⁹-tetrahydrocannabinol is present in said composition in concentrations ranging from 0.224% w/w (±0.063) to 4.883% w/w (±0.224).

8. The pharmaceutical composition of claim 7 wherein said Δ⁹-tetrahydrocannabinol is present in pharmaceutically pure form.

9. The pharmaceutical composition of claim 7 wherein the concentration of Δ⁹-tetrahydrocannabniol is sufficient to achieve serum concentration levels in a patient of 10–100 ng/ml fifteen minutes following inhalation.

10. The pharmaceutical composition of claim 7 wherein said organic solvent is ethanol.

11. The pharmaceutical composition of claim 7 wherein said organic solvent is 0% w/w of said stable composition.

12. The pharmaceutical composition of claim 7 wherein said stable composition is surfactant free.

* * * * *